United States Patent [19]

Naito et al.

[11] 4,324,784
[45] Apr. 13, 1982

[54] PROCESS FOR PREVENTING GROWTH OF MARINE ORGANISMS ON A SUBSTANCE USING HYDROGEN PEROXIDE

[75] Inventors: Akira Naito, Kashiwa; Toru Hayakawa, Chiba; Masakatsu Nakanishi, Sakai; Sunao Ikuta, Tokorozawa; Shoichiro Kajiwara, Matsudo; Hitoshi Yamaguchi, Yokkaichi, all of Japan

[73] Assignee: Mitsubishi Gas Chemical Company, Inc., Tokyo, Japan

[21] Appl. No.: 131,631

[22] Filed: Mar. 19, 1980

[51] Int. Cl.$^3$ .................... A01N 59/00; A01N 43/84; A01N 43/40; A01N 43/48
[52] U.S. Cl. .................... 424/130; 424/149; 424/246; 424/263; 424/269; 424/273 R; 424/300; 424/327; 424/329
[58] Field of Search ........... 424/130, 149, 263, 273 R, 424/327, 329, 300, 269, 246

[56] References Cited

U.S. PATENT DOCUMENTS

| 2,917,428 | 12/1959 | Hitzman | 424/130 |
| 3,082,146 | 3/1963 | Wentworth et al. | 424/130 |

FOREIGN PATENT DOCUMENTS

| 408927 | 1/1945 | Italy | 424/130 |
| 46-35867 | 10/1971 | Japan | 424/130 |
| 52-48258 | 4/1977 | Japan | 424/130 |

*Primary Examiner*—Douglas W. Robinson
*Attorney, Agent, or Firm*—Frishauf, Holtz, Goodman & Woodward

[57] ABSTRACT

A process for preventing growth of marine animals, i.e. shellfish, Polyzoa, and Hydrozoa on a surface, characterized by supplying hydrogen peroxide and/or a hydrogen peroxide-generating agent into sea water in contact with the surface is disclosed. Surfaces of apparatus and/or pipe constituting flow paths for sea water and plant utilizing sea water are kept clean by the process.

6 Claims, No Drawings

PROCESS FOR PREVENTING GROWTH OF MARINE ORGANISMS ON A SUBSTANCE USING HYDROGEN PEROXIDE

BACKGROUND OF THE INVENTION

This invention relates to a process for preventing growth of marine organisms on the surface of apparatus and/or pipe constituting flow path for sea water and plant utilizing sea water.

Industrial utilization of sea water has increased considerably. For example, much sea water is being used in steam power plants, iron-making works and in the petrochemical industry. Sea water is also being used for cooling ship condensers. Trouble caused by marine organisms, such as shellfish (mussels, barnacles, etc.), Polyzoa and Hydrozoa can not be disregarded. When such marine organisms adhere to the surface of pipe and/or plant constituting a flow path and grow thereon, the flow path of the pipe and/or plant becomes narrower. When many marine organisms adhere to the surface, some come off the surface and enter the condenser of the boiler and heat exchanger, thereby lowering the cooling efficiency thereof. Clogging of condenser tubes by particles from the surface gives rise to turbulent flow of the sea water, and the flow accelerates corrosion of metal.

A chlorine-generating agent, an organic tin compound, an organic sulfur compound, and a quaternary ammonium salt have been used in order to prevent such trouble. However, such agents have residual toxicity and accumulate in sea water. It is believed that large accumulations of such agents break the ecological system of the sea. For example, in order to prevent growth of marine organisms on a surface by adding chlorine and/or a chlorine generating agent to sea water, the agent must be used so as to provide concentration of resident chlorine and/or hypochlorite in sea water in the range of 0.1–0.2 ppm. Therefore, 1–2 ppm of available chlorine must be continuously added to the sea water in contact with the surface. Similarly, in case of using an organic tin compound, the compound must be continuously or intermittently added to the sea water so as to provide a concentration of the resident compound in the sea water in the range of 0.005–0.5 ppm. In case of using an organic sulfur compound, the compound must be continuously or intermittently added to the sea water so as to provide a concentration of the resident compound in sea water in the range of 1–10 ppm. In addition, when using chlorine, transportation of chlorine is dangerous and it is difficult to safely supply chlorine to the sea water.

Therefore, development of an agent to substitute for the chlorine-generating agents, the organic tin compounds, the organic sulfur compound or the quaternary ammonium salts, has long been desired, and research for reducing the amount of these agents when they are employed has been carried out.

SUMMARY OF THE INVENTION

The inventors of this invention carried out research to find a process for preventing growth of marine organisms on a surface using an agent having no residual toxicity and which is not accumulated in sea water. We found that hydrogen peroxide satisfied the above requirements. We also found that when hydrogen peroxide is continuously or intermittently used in combination with one or more of the prior agents, the amount of the prior agent employed can be reduced as a result of the synergistic effect derived from the combination of hydrogen peroxide and the prior agent.

An object of this invention is to provide a process for preventing growth of marine organisms on a surface, characterized by using a chemical agent having no residual toxicity, namely hydrogen peroxide.

Another object of this invention is to provide a process for controlling adhesion of marine organisms without disrupting the ecological system of the sea.

DETAILED DESCRIPTION OF THIS INVENTION

Hydrogen peroxide itself is not toxic and decomposes to form water and oxygen. So, hydrogen peroxide has no residual toxicity and is not accumulated in sea water. Therefore, hydrogen peroxide does not cause water pollution. When it is used in an appropriate amount and for an appropriate period, hydrogen peroxide can prevent growth of marine organisms on a surface or it can destroy the organisms.

Hydrogen peroxide may be continuously or intermittently supplied into sea water in contact with the surface. The amount of hydrogen peroxide to be employed and how to use hydrogen peroxide depend on nature of marine organisms, growing state of marine organisms, time of using hydrogen peroxide and economic effect. In general, the amount of hydrogen peroxide used is enough to give a concentration of hydrogen peroxide in sea water within the range of 0.01–500 ppm, preferably 0.05–100 ppm.

A hydrogen peroxide-generating agent having the same action as hydrogen peroxide can be used in the present invention. Examples of such hydrogen peroxide-generating agents include inorganic peroxo acids, such as peroxoboric acid, peroxocarbonic acid and the like; organic peroxo acids, such as peroxoacetic acid or salt thereof and adduct of urea and hydrogen peroxide. Chemical agents generating hydrogen peroxide in sea water can be used in the present invention.

Hydrogen peroxide and/or a hydrogen peroxide-generating agent can be used together with a second chemical agent selected from the group consisting of chlorine, an available chlorine-generating agent, a quaternary ammonium compound, hydrazine, a hydrazine-generating agent, an organic sulfur compound or mixtures thereof. In this case, the amount of the second agent to be employed can be reduced because a synergistic effect is derived from the combination of hydrogen peroxide and the second agent in comparison with the use of the second agent alone. Therefore, when hydrogen peroxide is used for such purpose, little water pollution by the second agent occurs. Particularly, when a combination of hydrogen peroxide and an available chlorine is used, oxygen in singlet state ($O^I$) is generated through oxidation-reduction reaction as shown in the following equation, and the oxygen can prevent growth of marine organisms on a surface

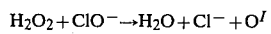

$$H_2O_2 + ClO^- \rightarrow H_2O + Cl^- + O^I$$

Examples of available chlorine-generating agents include hypochlorite, dichloro isocyanurate and the like, which generates chlorine in sea water. Examples of hydrazine-generating agents include hydrazine hydrochloride and hydrazine sulfate which generates hydrazine in sea water. Examples of quaternary ammonium compounds include, cetyltrimethyl ammonium chloride, lauryldimethylbenzyl ammonium chloride, laurylpyridinium chloride, 1-lauryl-2-methyl-3-imidazolium chloride and the like. Examples of organic sulfur compounds include thiurams, dithiocarbamates, thiazoles and the like. The organic sulfur compounds include, for example tetramethylthiuram disulfide, tetraethylthiuram disulfide, sodium dimethyldithiocarbamate, sodium diethyldithiocarbamate, 2-mercaptobenzo thiazole, 3,5-dimethyl-1,3,5,2H-tetrahydrothiadiazine-2-thion.

When hydrogen peroxide and/or a hydrogen peroxide-generating agent (sometimes hereinunder referred to as first chemical agent) is combined with the second chemical agent, the amount of the first chemical agent employed may be less than that of the first chemical agent when the first agent is used alone.

When a second chemical agent is used, it is combined with the first chemical agent so as to provide a concentration thereof in sea water within the following ranges:

| | |
|---|---|
| available chlorine | 0.01–1 ppm |
| hydrazine | 0.1–50 ppm |
| quaternary ammonium compound | 0.1–5 ppm |
| organic sulfur compound | 0.1–5 ppm |

The first chemical agent and the second chemical agent may be supplied into the sea water simultaneously, but it is preferred that the two chemical agents be supplied into the sea water alternately at a suitable interval. In general, the interval is in the range of 0 to 24 hours, preferably 0 to 12 hours and most preferably 0 to 6 hours.

According to the present invention, the growth of marine organisms on a surface in the flow path of sea water can be prevented by using hydrogen peroxide and/or a hydrogen peroxide-generating agent having no residual toxicity. According to the present invention, little water pollution in sea occurs and the sea's ecological system is not disrupted.

Furthermore, when hydrogen peroxide is combined with a second chemical agent, the amount of the second chemical agent employed will be less than what is required if the second agent is used alone.

The present invention is further illustrated by the following Examples. However, this invention should not be limited by these examples, and the changes and modification with the spirit and scope of this invention can be effected. Percent and part are by weight, unless otherwise specified.

EXAMPLE 1

This test was carried out through a period of from June to September which is the breeding season for shellfish, particularly barnacles. A test apparatus consisting of four columns made of glass and four pumps for supplying chemical agent was used, and the columns and pumps were arranged in parallel. 70 mm×40 mm plates of ground glass and 100 mm×50 mm wood pieces were placed in each column. Sea water was flowed through each column. Chemical agent was supplied into the column in concentration as given in Table 1. The number of shellfish, particularly barnacles adhering to the ground glass and wood pieces was observed after about 10 days. Ground glass and wood pieces in the column in which no chemical agent was supplied were similarly observed (control test). The chemical agent employed was a 35% aqueous solution of hydrogen peroxide. The agent was supplied continuously or intermittent into column. The results are shown in Table 1.

In Table 1, percent of control is as follows:

$$\text{Percent of control} = \frac{A - B}{A} \times 100$$

A ... number of marine organisms adhering when no chemical agent is added to the sea water B ... number of marine organisms adhering when chemical agent is added to the sea water

TABLE 1

| Conc. of $H_2O_2$ (ppm) | Supplying method | Percent of control ground glass | Percent of control wood pieces |
|---|---|---|---|
| 0 (control) | Continuous | 0 | 0 |
| 0.2 | | 41.4 | 40.1 |
| 0.5 | | 56.6 | 54.7 |
| 1 | | 65.9 | 63.3 |
| 2 | | 71.2 | 67.3 |
| 5 | | 84.3 | 80.9 |
| 10 | | 97.1 | 96.4 |
| 50 | | 98.4 | 97.7 |
| 100 | | 99.8 | 99.1 |
| 200 | | 100 | 100 |
| 300 | | 100 | 100 |
| 500 | | 100 | 100 |
| 5 | intermittent (1-hr continuous supply followed by 1-hr without supply) | 80.1 | 79.4 |
| 10 | intermittent (1-hr continuous supply followed by 1-hr without supply) | 92.9 | 90.8 |
| 50 | intermittent (1-hr continuous supply followed by 5-hrs without supply) | 96.9 | 96.3 |
| 100 | intermittent (1-hr continuous supply followed by 11-hrs without supply) | 98.1 | 97.5 |
| 200 | intermittent (1-hr continuous supply followed by 11-hrs without supply) | 99.6 | 98.8 |
| 300 | intermittent (1-hr continuous supply followed by 23-hrs without supply) | 100 | 100 |
| 500 | intermittent (1-hr continuous supply followed by 23-hrs without supply) | 100 | 100 |

Number of marine organisms adhering when hydrogen peroxide was not supplied in sea water was as follows:

| | |
|---|---|
| ground glass | $12 \times 10^4/m^2$ |
| wood pieces | $13 \times 10^4/m^2$ |

EXAMPLE 2

This test was carried out from May to October which is the breeding season for mussels. The same procedure as in Example 1 was repeated. The results are shown in Table 2.

TABLE 2

| Conc. of $H_2O_2$ (ppm) | Supplying method | Percent of control ground glass | Percent of control wood pieces |
|---|---|---|---|
| 0 (control) | continuous | 0 | 0 |
| 2 | | 73.4 | 71.1 |
| 5 | | 87.9 | 89.3 |
| 10 | | 97.6 | 97.7 |
| 50 | | 99.8 | 98.1 |
| 100 | | 100 | 99.1 |

TABLE 2-continued

| Conc. of $H_2O_2$ (ppm) | Supplying method | Percent of control ground glass | wood pieces |
|---|---|---|---|
| 200 | | 100 | 100 |
| 300 | | 100 | 100 |
| 500 | | 100 | 100 |
| 5 | intermittent (1-hr continuous supply followed by 1-hr without supply) | 81.9 | 80.7 |
| 10 | intermittent (1-hr continuous supply followed by 1-hr without supply) | 94.6 | 94.1 |
| 50 | intermittent (1-hr continuous supply followed by 5-hrs without supply) | 95.9 | 96.1 |
| 100 | imtermittent (1-hr continuous supply followed by 11-hrs without supply) | 98.3 | 97.5 |
| 200 | intermittent (1-hr continuous supply followed by 11-hrs without supply) | 99.9 | 99.9 |
| 300 | intermittent (1-hr continuous supply followed by 23-hrs without supply) | 100 | 100 |
| 500 | intermittent (1-hr continuous supply followed by 23-hrs without supply) | 100 | 100 |

The number of marine organisms adhering when hydrogen peroxide was not supplied in sea water was follows:

| ground glass | $14 \times 10^4/m^2$ |
|---|---|
| wood pieces | $14.5 \times 10^4/m^2$ |

EXAMPLE 3

In this Example, hydrogen peroxide and hydrazine were used as chemical agents. The hydrazine was 50% hydrazine hydrate (50% $N_2H_4 \cdot H_2O$). The test apparatus was the same as that of Example 1. The results are shown in Table 3. The plus symbol in column of adhering state of Polyzoa shows that Polyzoa was adhered on the test sample, whereas the minus symbol in the column shows that Polyzoa was not adhered. The greater the number of plus symbols, the more Polyzoa adhered.

TABLE 3

| Run No. | $H_2O_2$ (first chemical agent) (ppm) | Hydrazine (second chemical agent) (ppm) | Supplying method | Percent of controlling marine organisms adhered to ground glass mussel | barnacle | Adhering state of Polyzoa |
|---|---|---|---|---|---|---|
| 1 (control) | 0 | 0 | | 0 | 0 | +++++ |
| 2 | 2 | 0.5 | Two agents were supplied continuously, simultaneously | 81.6 | 83.5 | ++ |
| | | 5 | | 96.3 | 93.9 | + |
| | | 10 | | 99.8 | 98.1 | − |
| 3 | 2 | 0.5 | First agent was supplied continuously for 1 hr, followed by no supply for 1 hr. Second agent was supplied continuously for 1 hr while supply of first agent was stopped. | 80.4 | 79.9 | ++ |
| | | 5 | | 90.5 | 91.4 | + |
| | | 10 | | 96.7 | 97.8 | − |
| 4 | 2 | 0.5 | First agent was supplied continuously for 1 hr, followed by no supply for 3 hrs. Supply of second agent started simultaneously with stoppage of supply of first agent, and continued for 1 hr, followed by no supply for 3 hrs. | 76.9 | 77.1 | +++ |
| | | 5 | | 86.5 | 88.8 | ++ |
| | | 10 | | 90.3 | 92.9 | + |
| | | 20 | | 95.4 | 94.7 | − |
| 5 | 5 | 0.5 | Same as No. 2 | 83.9 | 84.7 | ++ |
| | | 5 | | 97.7 | 98.1 | − |
| | | 10 | | 99.4 | 99.7 | − |
| 6 | 5 | 0.5 | Same as No. 3 | 86.4 | 87.9 | ++ |
| | | 5 | | 97.6 | 96.9 | − |
| | | 10 | | 98.8 | 99.1 | − |
| 7 | 5 | 0.5 | Same as No. 4 | 79.7 | 80.4 | ++ |
| | | 5 | | 90.6 | 91.4 | + |
| | | 10 | | 94.4 | 96.3 | − |
| | | 20 | | 99.9 | 99.9 | − |
| 8 | 2 | 0 | Continuous | 70.1 | 71.7 | ++++ |
| | | 0 | intermittent (1-hr continuous supply followed by 1-hr without supply) | 61.1 | 60.3 | ++++ |
| | | 0 | intermittent (1-hr continuous supply followed by 3-hrs without supply) | 50.5 | 53.1 | ++++ |
| 9 | 5 | 0 | Continuous | 87.7 | 89.9 | ++ |
| | | 0 | intermittent (1-hr continuous supply followed by 1-hr without supply) | 81.1 | 80.1 | +++ |
| | | 0 | intermittent (1-hr continuous supply followed by 3-hrs without supply) | 70.0 | 69.4 | ++++ |
| 10 | 0 | 0.5 | Continuous | 0 | 0 | +++++ |
| | | 5 | | 42.3 | 40.0 | +++++ |
| | | 10 | | 50.1 | 53.1 | +++++ |
| 11 | 0 | 0.5 | intermittent (1-hr continuous supply followed by 1-hr without supply) | 0 | 0 | +++++ |
| | | 5 | | 35.7 | 31.6 | +++++ |
| | | 10 | | 41.9 | 40.7 | +++++ |
| 12 | 0 | 0.5 | intermittent (1-hr continuous supply followed by 3-hrs without supply) | 0 | 0 | +++++ |
| | | 5 | | 27.9 | 26.3 | +++++ |

TABLE 3-continued

| Run No. | $H_2O_2$ (first chemical agent) (ppm) | Hydrazine (second chemical agent) (ppm) | Supplying method | Percent of controlling marine organisms adhered to ground glass | | Adhering state of Polyzoa |
|---|---|---|---|---|---|---|
| | | | | mussel | barnacle | |
| | | 10 | | 34.5 | 36.1 | +++++ |
| | | 20 | | 63.4 | 57.9 | ++++ |

Number of marine organisms adhering when no chemical agent was supplied was as follows:
mussel   $13 \times 10^4/m^2$
barnacle   $3 \times 10^4/m^2$ When hydrazine alone was used, percent of control was 63.4% (mussel) and 57.9% (barnacle) even in concentration of 20 ppm. In order to enhance percent of control, hydrazine with high concentration must be used. When hydrazine was combined with hydrogen peroxide, the percent of control was above 90% in hydrazine concentration of 5 ppm.

EXAMPLE 4

In this example, a combination of hydrogen peroxide and available chlorine was tested. The chlorine-generating agent employed was sodium hypochlorite (content of available chlorine of 12%). The test apparatus was the same as that of Example 1. The results are shown in Table 4.

TABLE 4

| Run No. | $H_2O_2$ (first chemical agent) (ppm) | Available chlorine (ppm) | Supplying method | Percent of control of adhering of marine organisms to ground glass | | Adhering state of Polyzoa |
|---|---|---|---|---|---|---|
| | | | | mussel | barnacle | |
| 1 (Control) | 0 | 0 | | 0 | 0 | +++++ |
| 2 | 2 | 0.05 | Two agents were supplied continuously. | 77.4 | 78.6 | +++ |
| | | 0.1 | | 89.9 | 90.7 | ++ |
| | | 0.3 | | 99.3 | 99.9 | — |
| | | 0.5 | | 100 | 100 | — |
| 3 | 5 | 0.05 | Two agents were supplied continuously. | 91.9 | 92.7 | + |
| | | 0.1 | | 99.3 | 99.9 | — |
| | | 0.05 | First agent was supplied continuously | 88.3 | 86.9 | ++ |
| | | 0.1 | for 1 hr, followed by no supply for | 94.4 | 93.1 | + |
| | | 0.3 | 1 hr. | 100 | 100 | — |
| | | 0.5 | Second agent was supplied continuously. | 100 | 100 | — |
| 4 | 10 | 0.05 | First agent was supplied continuously | 98.9 | 97.6 | — |
| | | 0.1 | for 1 hr, followed by no supply for | 100 | 100 | — |
| | | 0.3 | 3 hrs. Supply of second agent started simultaneously with stoppage of supply of first agent, and continued for 1 hr, followed by no supply for 3 hrs. | 100 | 100 | — |
| 5 | 0.2 | 8 | First agent was continuously supplied. | 93.7 | 93.1 | + |
| | 0.5 | 6 | Second agent was continuously supplied | 97.4 | 96.7 | — |
| | 1 | 3 | for 1 hr, followed by no supply for | 95.5 | 96.1 | — |
| | 2 | 1 | 23 hrs. | 87.0 | 88.8 | + |
| 6 | 2 | 0 | continuous | 70.1 | 71.7 | ++++ |
| | 5 | 0 | | 87.7 | 89.9 | ++ |
| | 5 | 0 | intermittent (1-hr continuous supply followed by 1-hr without supply) | 81.1 | 80.1 | +++ |
| | 10 | 0 | intermittent (1-hr continuous supply followed by 3-hrs without supply) | 80.3 | 82.9 | +++ |
| 7 | 0 | 0.05 | continuous | 24.7 | 20.1 | +++++ |
| | | 0.1 | | 77.7 | 80.1 | +++ |
| | | 0.3 | | 90.1 | 89.9 | ++ |
| | | 0.5 | | 87.6 | 89.9 | ++ |
| 8 | 0 | 0.05 | intermittent (1-hr continuous supply | 7.6 | 6.1 | +++++ |
| | | 0.1 | followed by 3-hrs without supply) | 30.3 | 28.6 | +++++ |
| | | 0.3 | | 71.3 | 72.5 | +++ |
| 9 | 0 | 8 | intermittent (1-hr continuous supply | 80.3 | 80.5 | ++ |
| | | 6 | followed by 23-hrs without supply) | 78.6 | 77.1 | ++ |
| | | 3 | | 73.2 | 72.0 | +++ |
| | | 1.5 | | 40.7 | 41.2 | +++ |

Number of marine organisms adhering when no chemical agent was supplied was as follows:
mussel   $13 \times 10^4/m^2$
barnacle   $3 \times 10^4/m^2$ In order to achieve percent of control of higher than 90% by using only available chlorine, available chlorine with concentration of more than 0.3 ppm is necessary. However, when available chlorine is combined with hydrogen peroxide, available chlorine in a concentration of 0.1 ppm achieves a percent of control higher than 90%.

EXAMPLE 5

In this example, a combination of hydrogen peroxide and a quaternary ammonium salt was tested. The apparatus employed was the same as that of Example 1. The results are shown in Table 5.

TABLE 5

| Run No. | $H_2O_2$ (1st agent) ppm | Quaternary ammonium salt kind | concentration (ppm) | Supplying method | Percent of control of adhering of marine organisms to ground glass mussel | barnacle | Adhering state of Polyzoa |
|---|---|---|---|---|---|---|---|
| 1 control | 0 | | 0 | | 0 | 0 | +++++ |
| 2 | 2 | (I) | 0.5 | Two agents were continuously supplied | 77.9 | 79.6 | +++ |
| | | | 1 | " | 80.3 | 83.1 | ++ |
| | | (II) | 0.5 | " | 79.6 | 76.3 | +++ |
| | | | 1 | " | 87.4 | 89.1 | + |
| | | (III) | 0.5 | " | 73.7 | 74.4 | ++ |
| | | | 1 | " | 78.3 | 79.9 | ++ |
| | | (IV) | 0.5 | " | 80.1 | 81.3 | + |
| | | | 1 | " | 88.6 | 89.9 | + |
| 3 | 5 | (I) | 0.5 | " | 92.4 | 93.3 | + |
| | | | 1 | " | 94.6 | 96.6 | — |
| | | | 3 | " | 98.1 | 99.1 | — |
| | | (II) | 0.5 | " | 93.6 | 95.1 | + |
| | | | 1 | " | 94.7 | 96.6 | — |
| | | | 3 | " | 98.8 | 99.7 | — |
| | | (III) | 0.5 | " | 76.6 | 79.1 | +++ |
| | | | 1 | " | 83.9 | 86.1 | + |
| | | | 3 | " | 91.7 | 93.4 | + |
| | | (IV) | 0.5 | " | 93.5 | 94.1 | + |
| | | | 1 | " | 94.4 | 95.3 | + |
| | | | 3 | " | 99.1 | 99.4 | — |
| 4 | 10 | (I) | 0.5 | " | 98.0 | 98.0 | — |
| | | | 1 | " | 98.6 | 98.1 | — |
| | | | 3 | " | 100 | 100 | — |
| | | | 5 | " | 100 | 100 | — |
| | | (IV) | 0.5 | " | 98.6 | 98.7 | — |
| | | | 1 | " | 99.9 | 99.9 | — |
| | | | 3 | " | 100 | 100 | — |
| | | | 5 | " | 100 | 100 | — |
| 5 | 2 | | 0 | continuous | 70.1 | 71.7 | ++++ |
| | 5 | | 0 | " | 87.7 | 89.9 | ++ |
| | 10 | | 0 | " | 97.6 | 97.1 | — |
| 6 | 0 | (I) | 0.5 | " | 26.7 | 29.9 | +++++ |
| | | | 1 | " | 37.7 | 33.4 | +++++ |
| | | | 3 | " | 62.3 | 66.6 | ++++ |
| | | | 5 | " | 77.6 | 80.1 | +++ |
| 7 | 0 | (II) | 0.5 | " | 28.1 | 29.9 | +++++ |
| | | | 1 | " | 40.3 | 43.1 | +++++ |
| | | | 3 | " | 63.3 | 69.9 | ++ |
| 8 | 0 | (III) | 0.5 | " | 20.0 | 18.5 | +++++ |
| | | | 1 | " | 25.3 | 24.4 | +++++ |
| | | | 3 | " | 48.5 | 46.6 | +++++ |
| 9 | 0 | (IV) | 0.5 | " | 29.9 | 30.6 | +++++ |
| | | | 1 | " | 39.5 | 40.7 | +++++ |
| | | | 3 | " | 63.5 | 64.9 | ++++ |
| | | | 5 | " | 69.4 | 70.1 | ++++ |

Note
(1) Quaternary ammonium salt
(I) cetyltrimethylammonium chloride
(II) lauryldimethylbenzylammonium chloride
(III) laurylpyridinium chloride
(IV) 1-lauryl-2-methyl-3-imidazolium chloride
(2) Number of marine organisms adhering to ground glass when no chemical agent was supplied was as follows:
Mussel $13 \times 10^4/m^2$
Barnacle $3 \times 10^4/m^2$

EXAMPLE 6

In this example, a combination of hydrogen peroxide and organic sulfur compound was tested. The test apparatus was the same as that of Example 1. The results are shown in Table 6.

TABLE 6

| Run No. | $H_2O_2$ (first chemical agent) (ppm) | Organic sulfur compound (second chemical agent) kind | concentration (ppm) | Supplying method | Percent of control of adhering of marine organisms to ground glass mussel | barnacle | Adhering state of Polyzoa |
|---|---|---|---|---|---|---|---|
| 1 | 2 | (I) | 0.5 | First agent was supplied | 86.2 | 89.1 | + |
| | | | 1 | continuously | 91.1 | 93.6 | — |
| | | | 2 | Second agent was supplied | 98.3 | 96.4 | — |
| | | (II) | 0.5 | continuously for 1 hr per day | 80.3 | 81.6 | ++ |
| | | | 1 | | 87.1 | 88.9 | + |
| | | | 2 | | 90.3 | 91.5 | + |
| | | (III) | 0.5 | | 85.3 | 88.6 | + |
| | | | 1 | | 90.3 | 91.4 | — |

TABLE 6-continued

| Run No. | H$_2$O$_2$ (first chemical agent) (ppm) | Organic sulfur compound (second chemical agent) kind | concentration (ppm) | Supplying method | Percent of control of adhering of marine organisms to ground glass mussel | barnacle | Adhering state of Polyzoa |
| --- | --- | --- | --- | --- | --- | --- | --- |
|  |  |  | 2 |  | 94.3 | 96.6 | — |
| 2 | 5 | (I) | 0.5 |  | 95.1 | 96.2 | — |
|  |  |  | 1 |  | 99.0 | 98.4 | — |
|  |  |  | 2 |  | 100 | 100 | — |
|  |  | (III) | 0.5 |  | 94.4 | 93.8 | — |
|  |  |  | 1 |  | 99.0 | 99.7 | — |
|  |  |  | 2 |  | 100 | 100 | — |
| 3 | 10 | (I) | 0.5 | First agent was supplied | 99.9 | 99.6 | — |
|  |  |  | 1 | continuously | 100 | 100 | — |
|  |  |  | 2 | Second agent was supplied | 100 | 100 | — |
| 4 (control) | 0 |  | 0 | continuously for 1 hr per day | 0 | 0 | +++++ |
| 5 | 2 |  | 0 | First agent was supplied | 70.1 | 71.7 | ++++ |
|  | 5 |  | 0 | continuously | 87.7 | 89.9 | ++ |
|  | 10 |  | 0 |  | 97.6 | 97.1 | — |
| 6 | 0 | (I) | 0.5 | Second agent was supplied | 23.6 | 27.7 | +++++ |
|  |  |  | 1 | continuously for 1 hr per day | 43.6 | 49.9 | +++++ |
|  |  |  | 2 |  | 70.3 | 71.8 | ++++ |
| 7 | 0 | (II) | 0.5 |  | 11.1 | 15.3 | +++++ |
|  |  |  | 1 |  | 20.6 | 17.9 | +++++ |
|  |  |  | 2 |  | 40.1 | 46.7 | +++++ |
| 8 | 0 | (III) | 0.5 | Second agent was supplied | 27.8 | 26.9 | +++++ |
|  |  |  | 1 | continuously for 1 hr per day | 49.1 | 50.3 | +++++ |
|  |  |  | 2 |  | 71.1 | 72.8 | ++++ |

Note:
(1) Organic sulfur compound
(I) sodium dimethyldithiocarbamate
(II) 2-mercaptobenzothiazol
(III) 3,5-dimethyl-1,3,5,2H-tetrahydrothiadiazine-2-thion
(2) Number of marine organisms adhered to ground glass when no chemical agent is supplied was as follows:
mussel    13 × 10$^4$/m$^2$
barnacle   3 × 10$^4$/m$^2$

What is claimed is:

1. A process for preventing growth of shellfish, Polyzoa and Hydrozoa on a manufactured surface of an industrial plant in contact with sea water, characterized by adding a compound selected from the group consisting of hydrogen peroxide, an inorganic peroxo acid and an organic peroxo acid to the sea water in contact with said surface to provide a concentration of hydrogen peroxide in said sea water in an amount of from 0.01 to 500 ppm.

2. The process of claim 1 wherein chlorine, a hypochlorite or dichloro isocyanurate is also added to said sea water to provide a concentration thereof in said sea water of from 0.01 to 1 ppm.

3. The process of claim 1 wherein hydrazine, hydrazine hydrochloride, or hydrazine sulfate is also added to said sea water to provide a concentration thereof in said sea water of from 0.1 to 50 ppm.

4. The process of claim 1 wherein cetyltrimethyl ammonium chloride, laurylpyridinium chloride or 1-lauryl-2-methyl-3-imidazolium chloride is also added to said sea water to provide a concentration thereof in said sea water of from 0.1 to 5 ppm.

5. The process of claim 1 wherein tetramethylthiuram disulfite, tetraethylthiuram disulfide, sodium dimethyldithiocarbamate, sodium diethyldithiocarbamate, 2-mercaptobenzothiazole or 3,5-dimethyl-1,3,5,2H-tetrahydrothiadiazine-2-thion is also added to said sea water to provide a concentration thereof in said sea water of from 0.1 to 5 ppm.

6. The process of claim 1 wherein hydrogen peroxide is utilized as said compound.

* * * * *